(12) United States Patent
Stray

(10) Patent No.: US 8,895,484 B2
(45) Date of Patent: Nov. 25, 2014

(54) USE OF BIPHENYL, TERPHENYL, AND FLUORENE SULPHONIC ACID BASED TRACERS FOR MONITORING STREAMS OF FLUIDS

(75) Inventor: Helge Stray, Hagan (NO)

(73) Assignee: Restrack AS, Kjeller (NO)

( * ) Notice: Subject to any disclaimer, the term of this patent is extended or adjusted under 35 U.S.C. 154(b) by 1473 days.

(21) Appl. No.: 12/305,275

(22) PCT Filed: Jun. 19, 2007

(86) PCT No.: PCT/NO2007/000215
§ 371 (c)(1),
(2), (4) Date: Aug. 12, 2009

(87) PCT Pub. No.: WO2007/148981
PCT Pub. Date: Dec. 27, 2007

(65) Prior Publication Data
US 2010/0016181 A1    Jan. 21, 2010

(30) Foreign Application Priority Data
Jun. 20, 2006  (NO) .................................. 20062891

(51) Int. Cl.
*E21B 47/04* (2012.01)
*E21B 47/09* (2012.01)
*E21B 47/10* (2012.01)
*G01N 33/28* (2006.01)
*G01N 33/18* (2006.01)

(52) U.S. Cl.
CPC ........ *G01N 33/2823* (2013.01); *G01N 33/1826* (2013.01)
USPC ........... 507/264; 507/241; 507/259; 507/260; 507/263; 507/267; 166/250.01; 166/336

(58) Field of Classification Search
None
See application file for complete search history.

(56) References Cited

U.S. PATENT DOCUMENTS

| 2,708,155 | A | * | 5/1955 | Buckley et al. | ................. 436/28 |
| 2,725,283 | A | * | 11/1955 | Mounce et al. | ................. 422/50 |
| 2,740,695 | A | * | 4/1956 | Buckley et al. | ................. 436/28 |
| 3,341,319 | A | * | 9/1967 | Hibbard | ........................ 504/354 |

(Continued)

FOREIGN PATENT DOCUMENTS

| CA | 594807 A | 3/1960 |
| EP | 0 624 798 A | 11/1994 |

(Continued)

OTHER PUBLICATIONS

Rose, P.E. et al.: "Tracer Testing at Dixie Valley, Nevada, Using Pyrene Tetrasulfonate, Amino G, and Fluorescein" *Transactions*, vol. 22, Sep. 20-23, 1998, pp. 583-587.

(Continued)

*Primary Examiner* — John J Figueroa
(74) *Attorney, Agent, or Firm* — Frommer Lawrence & Haug LLP; Ronald R. Santucci

(57) ABSTRACT

Biphenylmono- and polysulphonic acids and salts thereof, fluorenemono- and polysulphonic acids and salts thereof as well as p-terphenylmono- and polysulphonic acids and salts thereof may be used successfully as tracers for surveying, monitoring and/or measuring movements of aqueous fluids in aqueous and/or non-aqueous media. Said substances are especially suited for surveying or monitoring movements of fluids in oil wells or reservoirs as well as for fluid movements in hydrothermal reservoirs.

17 Claims, 11 Drawing Sheets

Structural formula for biphenyldisulphonic acids

Structural formula for fluorenedisulphonic acids

Structural formula for p-terphenyltrisulphonic acids

(56) References Cited

U.S. PATENT DOCUMENTS

| | | | |
|---|---|---|---|
| 3,442,921 | A | 5/1969 | Grant et al. |
| 4,264,329 | A | 4/1981 | Beckett |
| 4,555,489 | A | 11/1985 | Schmitt |
| 5,246,860 | A | 9/1993 | Hutchins et al. |
| 6,780,305 | B2 * | 8/2004 | Nishino et al. ............... 205/658 |
| 2001/0036667 | A1 | 11/2001 | Tayebi et al. |
| 2002/0160308 | A1 * | 10/2002 | Nishino et al. ............. 430/271.1 |
| 2005/0025659 | A1 * | 2/2005 | Godfrey et al. .................... 422/1 |
| 2005/0205256 | A1 * | 9/2005 | DiFoggio ................. 166/250.16 |
| 2005/0224258 | A1 * | 10/2005 | Fincher et al. .................. 175/57 |

FOREIGN PATENT DOCUMENTS

| | | |
|---|---|---|
| EP | 1 464 724 A | 10/2004 |
| GB | 829243 | 3/1960 |
| WO | WO 2005/016479 A | 2/2005 |
| WO | WO 2005/100746 A | 10/2005 |
| WO | WO 2006/004426 A | 1/2006 |

OTHER PUBLICATIONS

Tallberg, Petra et al.: "Germanium-68 as a tracer for silicon fluxes in freshwater sediment", *Water Research*, 36 (2002), pp. 956-962.

Voronkov, Mikhail G. et al.: "Genesis and evolution in the chemistry of organogermanium, organotin and organolead compounds", *The chemistry of organic germanium, tin and lead compounds*, vol. 2, 2002 (Chapter 1, pp. 1-130).

Behrens, H. et al.: "Toxicological and ecotoxicological assessment of water tracers", *Hydrogeology Journal*, 2001, 9, pp. 321-325.

Kuhn, Eberhardt et al.; "GC Analysis of Polybrominated Flame Retardants", Agilent Technologies, Sep. 11, 2003.

Search Report issued by Norwegian Patent Office for related Norwegian application 20092881 dated Feb. 4, 2014.

Search Report issued by Norwegian Patent Office for related Norwegian application 20090281 dated Jan. 30, 2014.

* cited by examiner

Figure 12
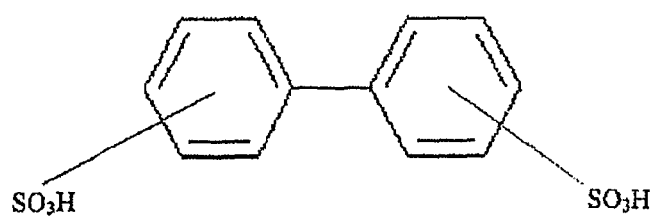
Structural formula for biphenyldisulphonic acids
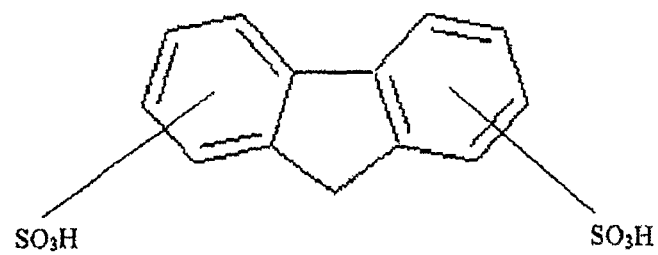
Structural formula for fluorenedisulphonic acids
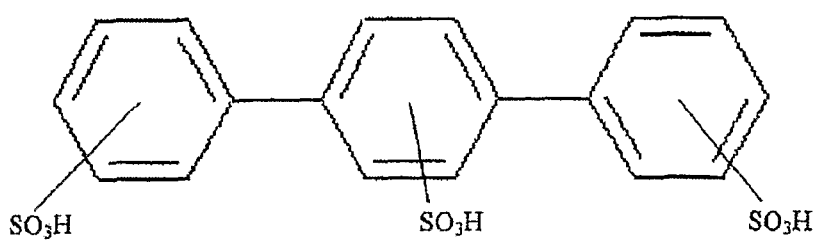
Structural formula for p-terphenyltrisulphonic acids

USE OF BIPHENYL, TERPHENYL, AND FLUORENE SULPHONIC ACID BASED TRACERS FOR MONITORING STREAMS OF FLUIDS

This application is a 371 of PCT/NO2007/000215 filed on Jun. 19, 2007, published on Dec. 27, 2007 under publication number WO 2007/148981 A which claims priority benefits from Norwegian Patent Application No. 2006 2891 filed Jun. 20, 2006, the disclosure of which is incorporated herein by reference.

The present invention concerns polyaromatic sulphonic acids suitable as tracers for measuring or monitoring petrol reservoirs, ground water basins or industrial processes as well as organic germanium compounds as tracers for measuring or monitoring gas or fluid streams in oil and gas reservoirs.

The measurement of movement in fluids, optionally the detection of leaks or some other form of fluid movement is of great importance within the maintenance/surveillance of fluid reservoirs such as oil and gas reservoirs or in measuring movement in ground water.

Previously known detection materials are known from U.S. Pat. No. 5,246,860 of September 1993 in the name of Hutchins et al. Other types of techniques are known from Crescenzi, C., DiCorcia, A., Marcomini, A., Pojana, G., Samperi, R., "Method development for trace determination of poly(naphthalenesulphonate)-type pollutants in water by liquid chromatography-electrospray mass spectrometry", J. Chromatogr. A, 923 (2001) 97-105.

Rose, P. E., Johnson, S. D., Kilbourn, P., Kasteler, C., "Tracer testing at Dixie Valley, Nev. using 1-naphthalene sulphonate and 2,6-naphthalene disulphonate", Proceedings, Twenty-Seventh Workshop in Geothermal Reservoir Engineering Stanford University, Stanford, Calif., Jan. 28-30, 2002.

Voronkov, M. G., Abzaeva, K. A., "Genesis and evolution in the chemistry of organogermanium, orgnanotin and organolead compounds" in "The chemistry of organic compounds of Germanium, Tin and Lead", edited by Rappaport, Z., John Wiley & Sons, 2002, ISBN 0-471-49738-X.

AMBIT OF THE INVENTION

Three families of organic tracer compounds are proposed for monitoring movements of water. The tracers can be used for monitoring water movement in different applications, such as for studying eater movement in petroleum reservoirs, in geothermal reservoirs, in surface and subterranean hydrological studies and in industrial processes. The three groups of tracers are biphenylsulphonic acids, fluorenesulphonic acids, p-terphenylsulphonic acids and salts of these compounds. In addition the invention includes the compounds mentioned above where one or more of the hydrogen atoms in the ring system is substituted by one or more amino, hydroxy and/or methyl groups.

In a further aspect the invention concerns the use of two groups of chemical compounds for measuring and monitoring movement in water-based fluids in petrol reservoirs, in geothermic reservoirs, in ground water and in connection with industrial processes. The group of trace substances is biphenylic sulphonic acids and fluorene sulphonic and salts of these compounds. Additionally the invention comprises the use of such compounds wherein a hydrogen atom in one of the aromatic rings has been exchanged for either an amino group or a hydroxy group. Biphenyl sulphonic acids and fluorene sulphonic acids are stable at elevated temperatures and may be measured in water down to very low concentrations through the aid of liquid chromatography and fluorescence detection.

BACKGROUND OF THE INVENTION

The present invention relates to three families of organic chemical compounds for monitoring movements of water solutions such as monitoring subterranean movements of fluids in petroleum and hydrothermal reservoirs. The term subterranean is meant to cover all aqueous-based fluids such as formation water, production water or liquids injected into oil and gas reservoirs as well as ground water and geothermal brines. In addition, the invention includes the application of the three families of chemicals in any industrial process where movement of water or aqueous solutions is monitored, for instance in tracer studies for monitoring the movement of 1,2-ethanediol used for drying natural gas in gas pipes from oil and gas wells.

The invention also concerns the use of two groups of chemical compounds for measuring and/or monitoring movements in sub-aqueous currents or streams e.g. in connection with well-to-well investigations of petrol and oil well reservoirs or geothermic reservoirs. The notion sub-water or sub-aqueous streams or currents covers all water-based fluids such as formation water, production is water injected into petrol or oil reservoirs, ground water and geothermic brines. Additionally the invention comprises the use of these two groups of chemical substances in any industrial process where it is an object to monitor, follow or map the movements of liquid streams or currents such as in trace element monitoring for measuring the movement of 1,2-ethanediol or other chemical substances used for drying natural gas from petrol or oil reservoirs.

Institute for Energy Technology (IFE) has since the nineteen sixties worked with the development of trace substances for industrial purposes. Since the beginning of the nineteen eighties the business has focused on the oil and gas industry. The main object of inter-well (well-to-well) trace element investigations is to map or monitor the stream flux or regions in the reservoir and to measure qualitatively and quantitatively the flux or stream connections between the injection and production wells. The data from the trace element monitoring in combination with ordinary production data, pressure measurements and information from well logging provide the best available basis for evaluating the pattern for the dynamic fluid streams and thereby the optimal extraction and processing of the reservoir. Due to environmental considerations radioactive trace substances have been replaced with chemical, mainly organic, trace substances, e.g. fluorinated benzoic acids in trace substance investigations performed by IFE. The environmental authorities in Norway have indicated that the use of fluorinated benzoic acids gradually should be phased out and become replaced with more environmentally friendly trace substances. There is also a continuous demand for new trace substances to be used in petrol and oil reservoirs and in geothermal reservoirs as the present tracers are gradually being used in many wells.

Rose et al. found that naphthalene sulphonates (NAS) are thermally stable and may be used as water tracers in geothermic reservoirs at temperatures up to 330° C. In an American patent Hutchins et al. have disclosed the use of a number of trace substances in sub-water streams, e.g. some naphthalene sulphonic acids. These substances may be measured in very low concentrations (micrograms per cubic meters or ppt-levels) through the use of high pressure liquid chromatography with fluorescence detection (HPLC-FLD). These analytical techniques are relatively simple compared to methods that are used for trace analyses today (GC-MS, LC-MS, and ICP-MS). The NAS tracers have been tested at IFE for their suitability as water tracers in gas and oil reservoirs with good results. Through the aid of standardized environmental tests it has not been possible to detect that naphthalene sulphonic acids as trace substances have any negative effect on the environment. A problem with the use of naphthalene suphionic acids as trace substances has been that the wells may be polluted with the same substances. This is because the concrete that often is used in the wells contains an additive that is a polymerization product between 2-naphthalene sulphonate and formaldehyde. The additive will also contain a number of different isomeric compounds of naphthalene sulphonic acids that slowly leak from the concrete and into the production water. Additives of concrete containing polymeric 2-naphthalenesulphonate type compounds have been widely used in many oil and gas wells around the world, and this may contribute to a background level also of other isomers of NAS (Crescenzi et al.).

Tests performed at IFE have shown that 4,4'-biphenyl disulphonic acid has a corresponding stability as naphthalene sulphonic acid (NAS). As for naphthalene sulphonic acids there are reasons to believe that all of the isomeric compounds of biphenyl sulphonic acid have similar properties as 4,4'-biphenyl disulphonic acid with respect to thermal stability. Some compounds from the three groups have been synthesized at IFE. One of the fluorene sulphonic acids that were synthesized and identified was 2,4,7-fluorene trisulphonic acid. The level of interference from other organic compounds in produced water from some oil wells was investigated and found to be very low. This has made the detection down to a level below 10 µg/m$^3$ (ppt) possible in production water from these wells (FIGS. 9 and 10).

Representatives from all the three families of chemical compounds have the same high level of thermal stability as the NAS, though the thermal stability of fluorenesulphonic acids is somewhat lower than for the other two groups. Studies performed at IFE showed that the thermal stability of 4,4'-BDS was as good as for the NAS and that adsorption to rock material was low (FIG. 11). Some naphtalenemono- and naphthalenedisulphonic acids with one of the hydrogen atoms attached to the ring system substituted with either an amino or hydroxyl group have been tested for their suitability as water tracers at IFE. These groups of tracers have generally a lower thermal stability but can often be detected more selectively and at lower concentrations in a matrix of organic components present in water from oil reservoirs than the NAS. It is likely that the same will be the case for biphenyl-, fluorenesulphonic and p-terphenylsulphonic acids with one of the hydrogen atoms substituted by an amino or hydroxyl group.

4,4'-biphenyl sulphonic acid may be detected down to a level of 100 µg/m$^3$ (ppt) without any up-concentration in the production water from an oil field in the North Sea, and 10 µg/m$^3$ may be detected after up-concentration.

On account of the similarities between the polyaromatic hydrocarbons concerning chemical properties and thermal stability, it is expected that the fluroene sulphonic acids also have the same degree of thermal stability and detection capability as the naphthalene sulphonic acids and 4,4'-biphenyl disulphonic acid. Some naphthalene mono and naphthalene disulphonic acids, wherein one of the hydrogen atoms in the aromatic rings has been exchanged with an amine or a hydroxy group, have been tested with respect to their properties as tracers in petrol and oil reservoirs by IFE. These substances have proven to possess a lower thermal stability than the pure naphthalene sulphonic acids, but as a compensation they may in many cases be detected more specifically with respect to the background of other organic compounds that are present in production water from petrol and oil reservoirs, and they may also be measured at even lower concentrations. Representative members from all the three groups of chemical compounds have high thermal stability such as naphthalene sulphonic acids, even if the stability of fluorene sulphonic acids appear to be somewhat lower than for the other two groups. Studies performed at IFE have proven that the thermal stability of 4,4'-biphenyl disulphonic acid was equally good as for naphthalene sulphonic acids and that the adsorption to rock material was small (FIG. 11). Some naphthalene mono- and naphthalene disulphonic acids wherein one of the hydrogen atoms in the aromatic rings have been replaced with an amine or a hydroxy group, have been tested with respect to their properties as tracers in petrol and oil reservoirs by IFE. These compounds have been proven to possess lower thermal stability than the pure naphthalene sulphonic acids, but as a compensation they may in many cases be detected more specifically with respect to the background of other organic compounds that may be present in production water from petrol reservoirs and they may be detected at even lower concentrations. Consequently it is probable that the same is valid for biphenyl, fluorene and p-terphenyl sulphonic acids with a hydrogen atom exchanged for an amine or hydroxy group.

SUMMARY OF THE INVENTION

The present invention is directed towards the use of isomeric compounds of biphenyl sulphonic acids (isomers of biphenyl mono and biphenyl poly sulphonic acids, e.g. biphenyl di, biphenyl tri and biphenyl tetra sulphonic acids) and salts thereof as well as the corresponding groups of isomers of fluorene sulphonic acids and salts thereof and of the corresponding groups of isomers of p-terphenyl sulphonic acids and salts thereof as tracers for measuring and surveying water-based liquid streams. Additionally the invention comprises the same use of corresponding compounds wherein one or more hydrogen atoms have been replaced with either one or more amine, hydroxy and/or methyl groups.

DISCLOSURE OF FIGURES

Figure 1:
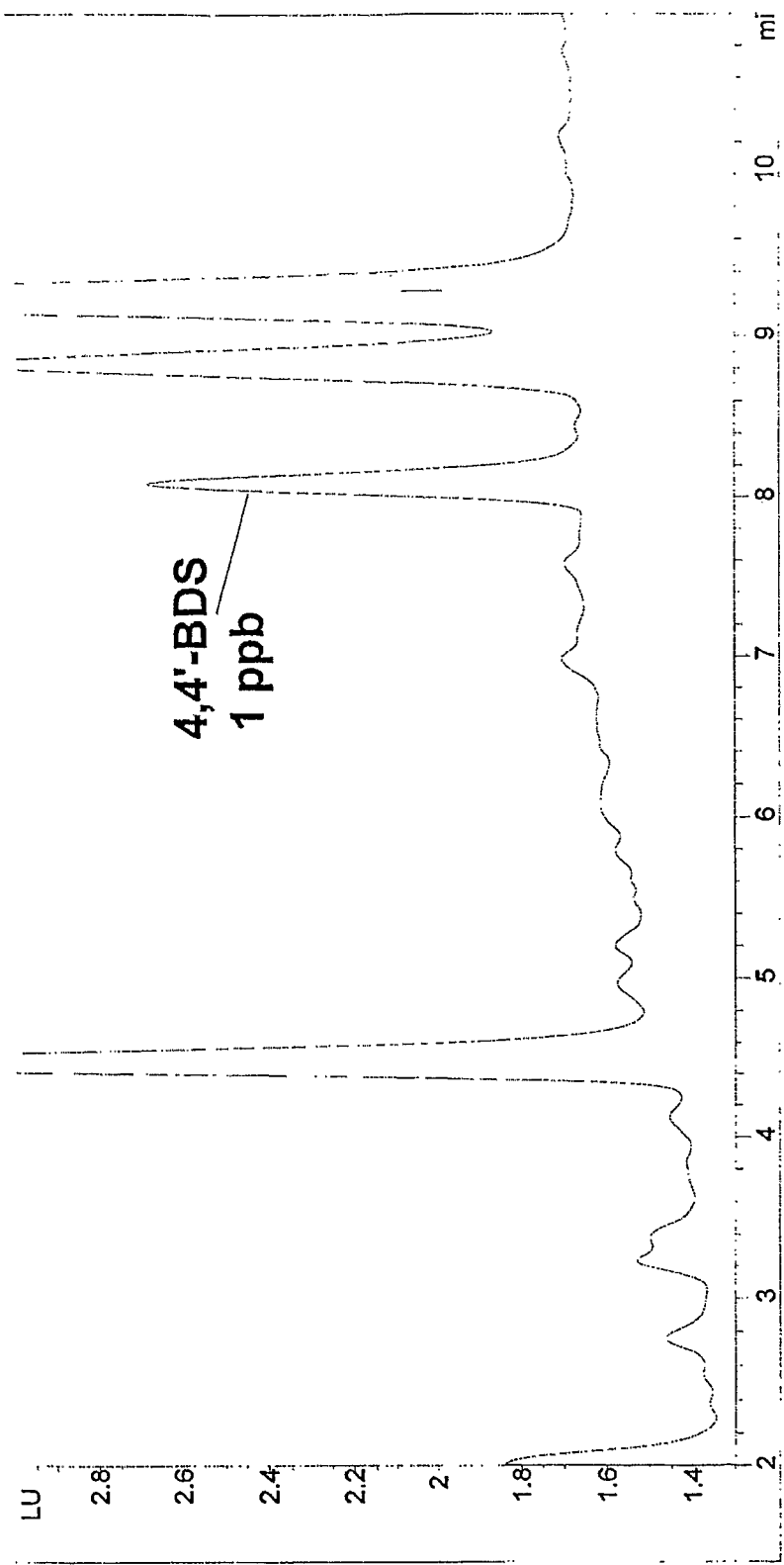
FIG. 1 shows a graphic representation of the retention time (x-axis) versus response from a fluorescence detector (y-axis) after HPLC-FLD analysis of produced water from an oil well added 1 µg 4,4'-biphenyl disulphonic acid disodium salt per liter (1 ppb).
Figure 2:
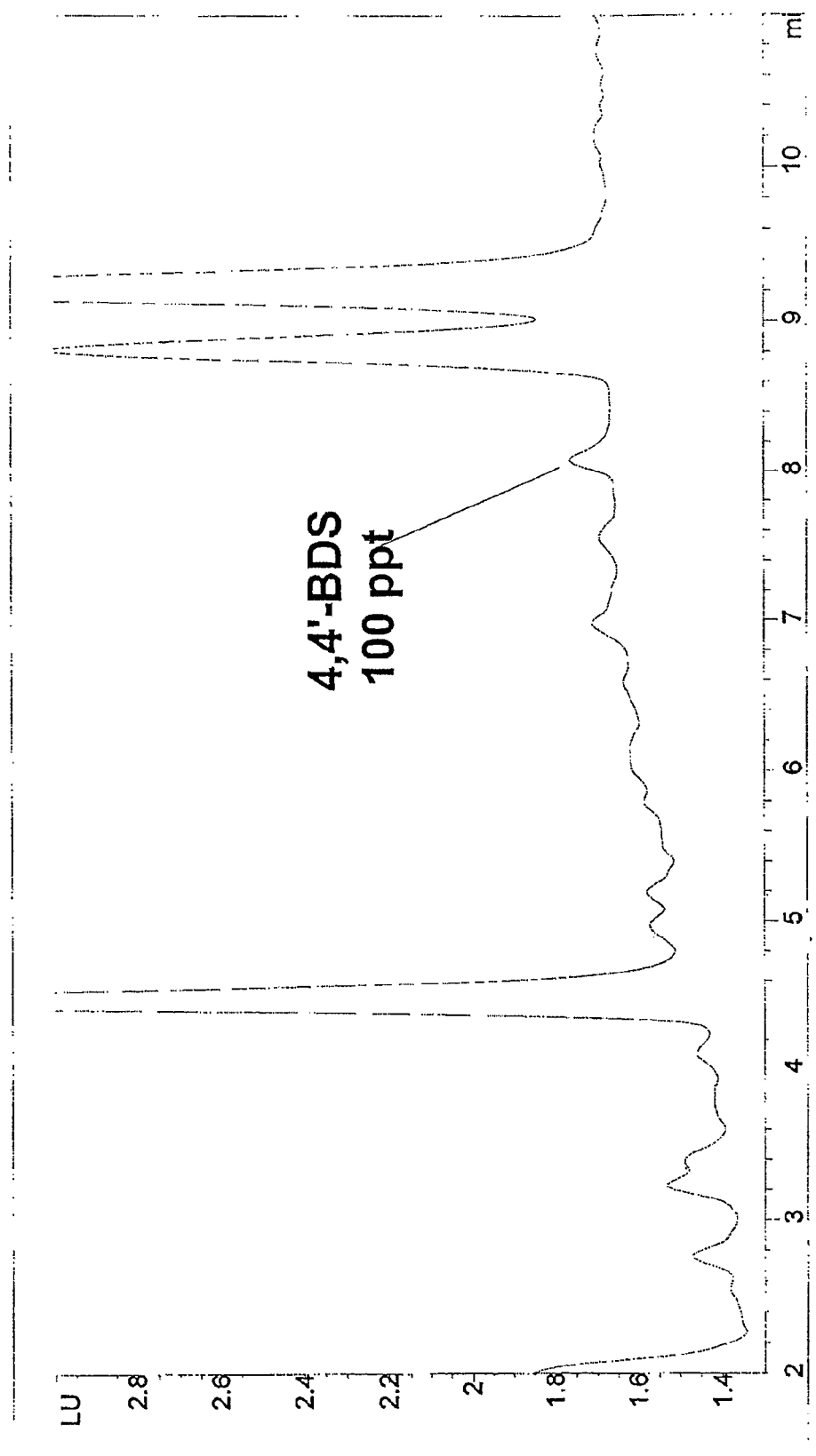
FIG. 2 shows a graphic representation of retention time (x-axis) versus response from the fluorescence detector (y-axis) after HPLC-FLD analysis of produced water from an oil well added 0.1 µg 4,4'-biphenyl disulphonic acid disodium salt per liter (100 ppt).
Figure 3:
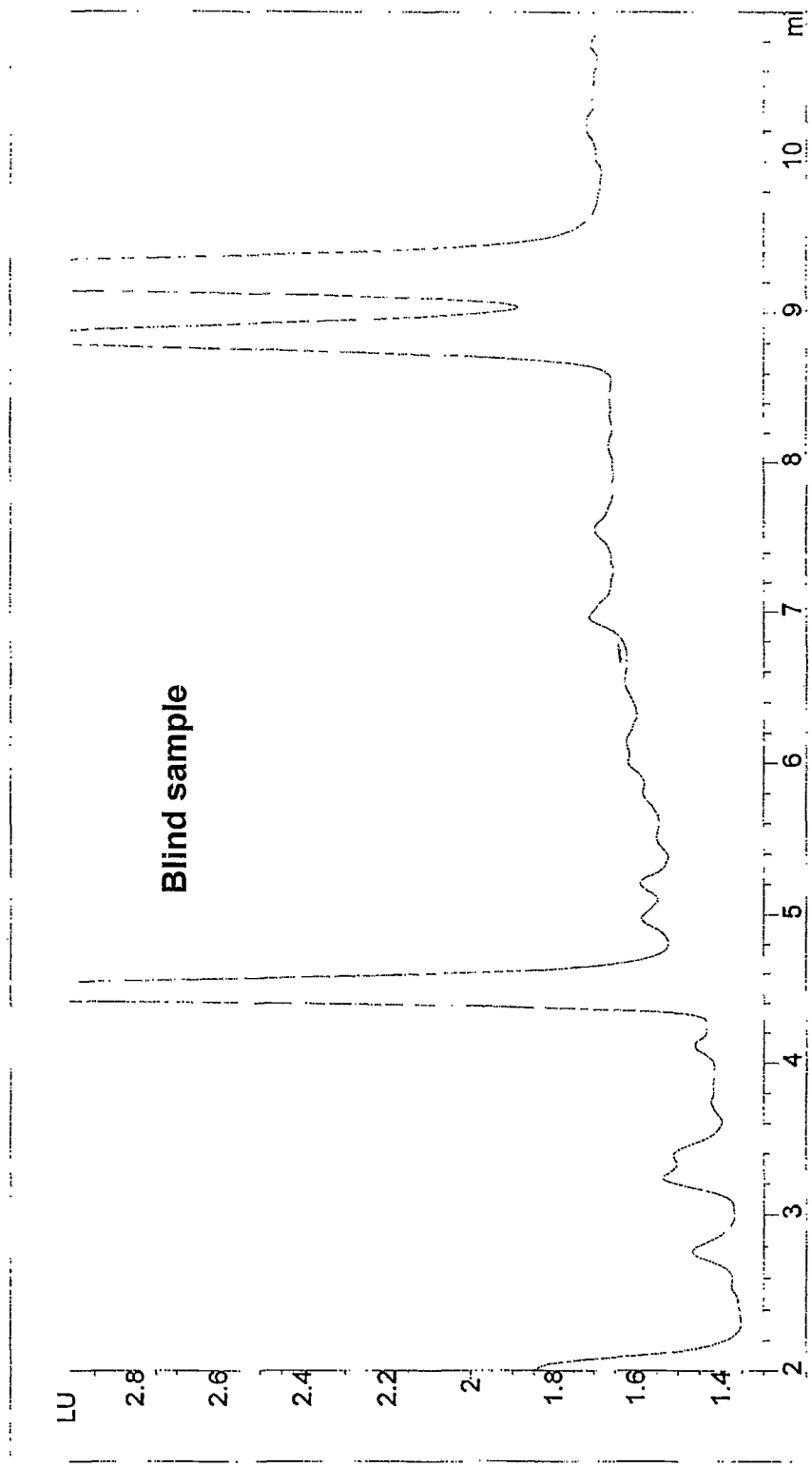
FIG. 3 shows a graphic representation of the retention time (x-axis) versus response from the fluorescence detector (y-axis) after HPLC-FLD analysis of produced water from an oil well without the addition of a tracer (blind sample).
Figure 4:
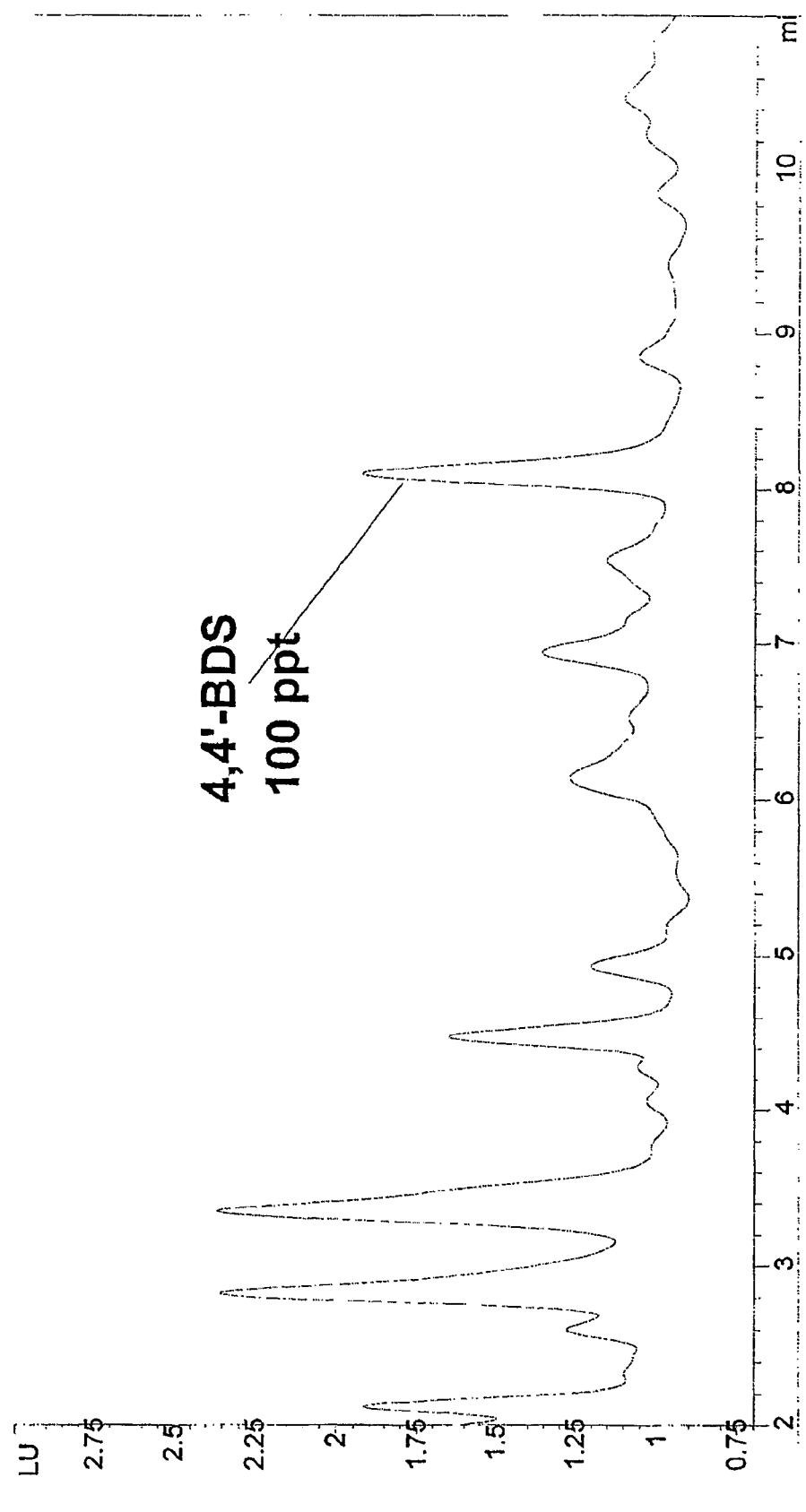
FIG. 4 shows a graphic representation of the retention time (x-axis) versus response from the fluorescence detector (y-axis) after HPLC-FLD analysis of produced water from an oil well added 0.1 µg of 4,4'-biphenyl disulphonic acid disodium salt per liter (100 ppt) after purification and up-concentration with a factor of 10.
Figure 5:
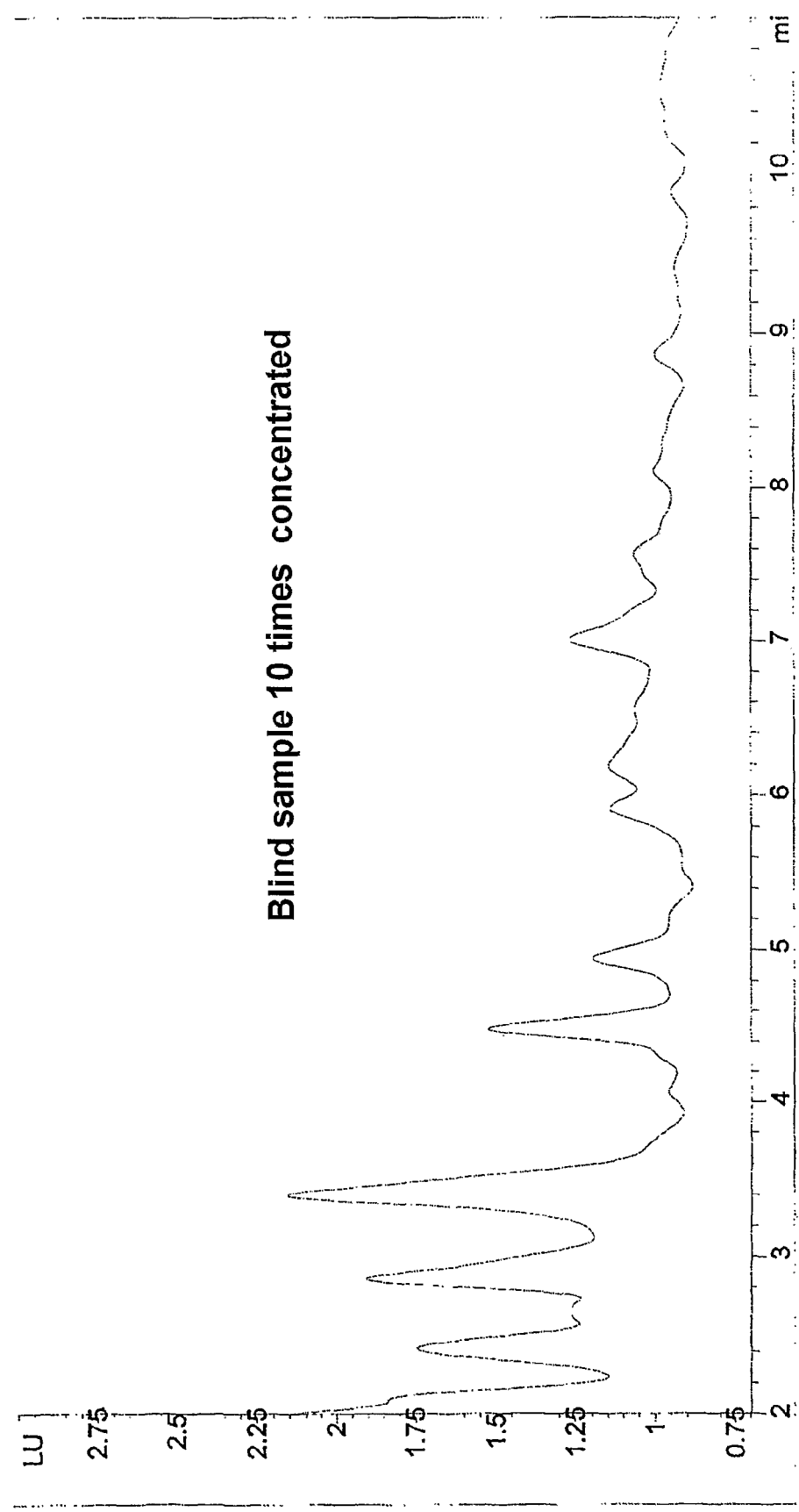
FIG. 5 shows a graphic representation of the retention time (x-axis) versus response from the fluorescence detector (y-axis) after HPLC-FLD analysis of produced water from an oil well without any addition of tracer (blind sample) after purification and up-concentration with a factor of 10.
Figure 6:
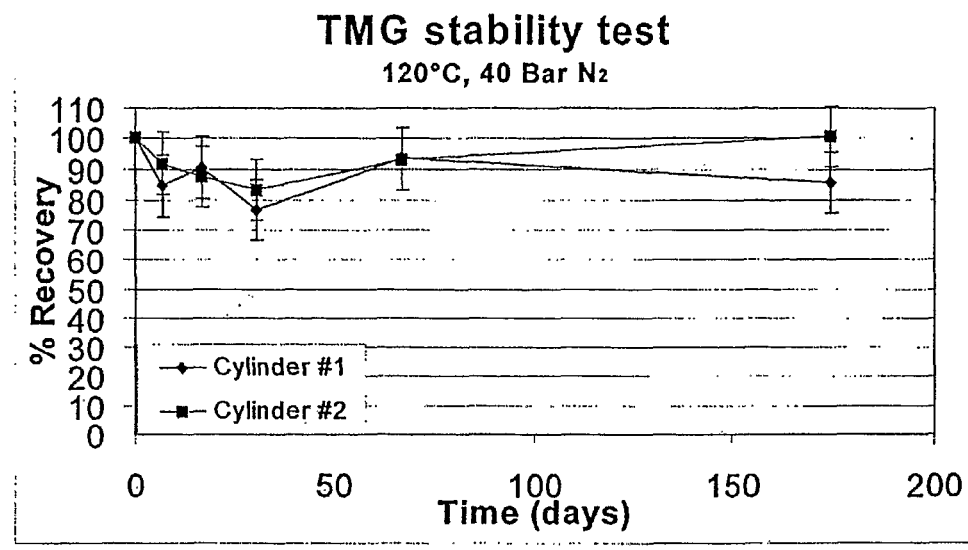

FIG. 6 is a graphic representation of percent redetection of TMG (y-axis) as a function of time (x-axis) in connection with stability tests of TMG. Two 1-liter steel cylinders were filled with 100 ml sand and 35 ml water and pressurized up to 40 bars with $N_2$. The temperature was set to 120° C. and the original concentration of TMG was 10-41/1 (100 ppm).

Figure 7:
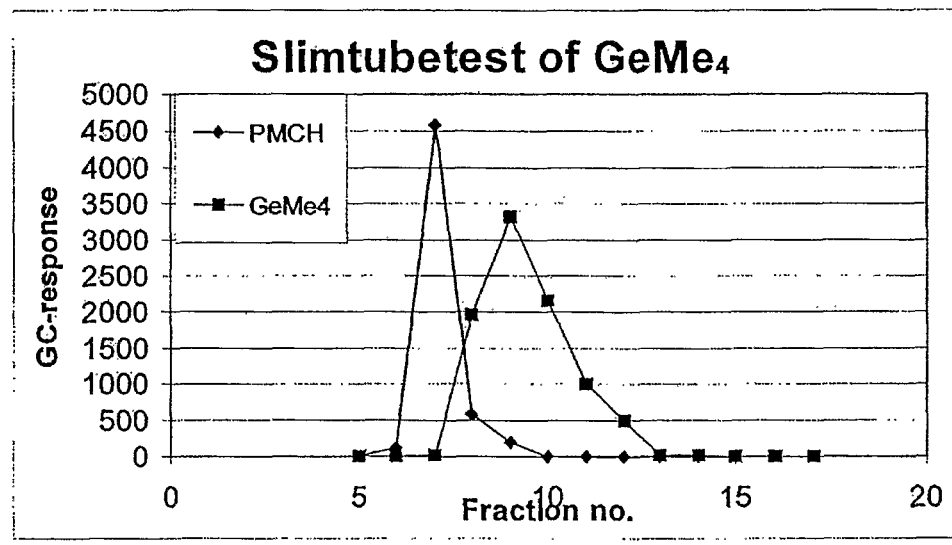

FIG. 7 shows a graphic representation of the gauge measurement of the gas chromatographic analysis of TMG and perfluorometyl cyclohexane (PMCH) being a commonly used tracer for gas today (y-axis) as a function of the fraction number. The fractions were retrieved and analysed at regular time intervals after injection of the two components in a stream of natural gas flowing through a pipe filled with Ottawa sand with 30% oil saturation at a temperature of 90° C. and a pressure of 150 bars. The display shows that TMG becomes somewhat retarded in comparison with PMCH, this indicating that the distribution coefficient for TMG towards oil i higher than the corresponding one for PMCH. TMG will still work as a tracer for gas at reservoir conditions.

Figure 8:
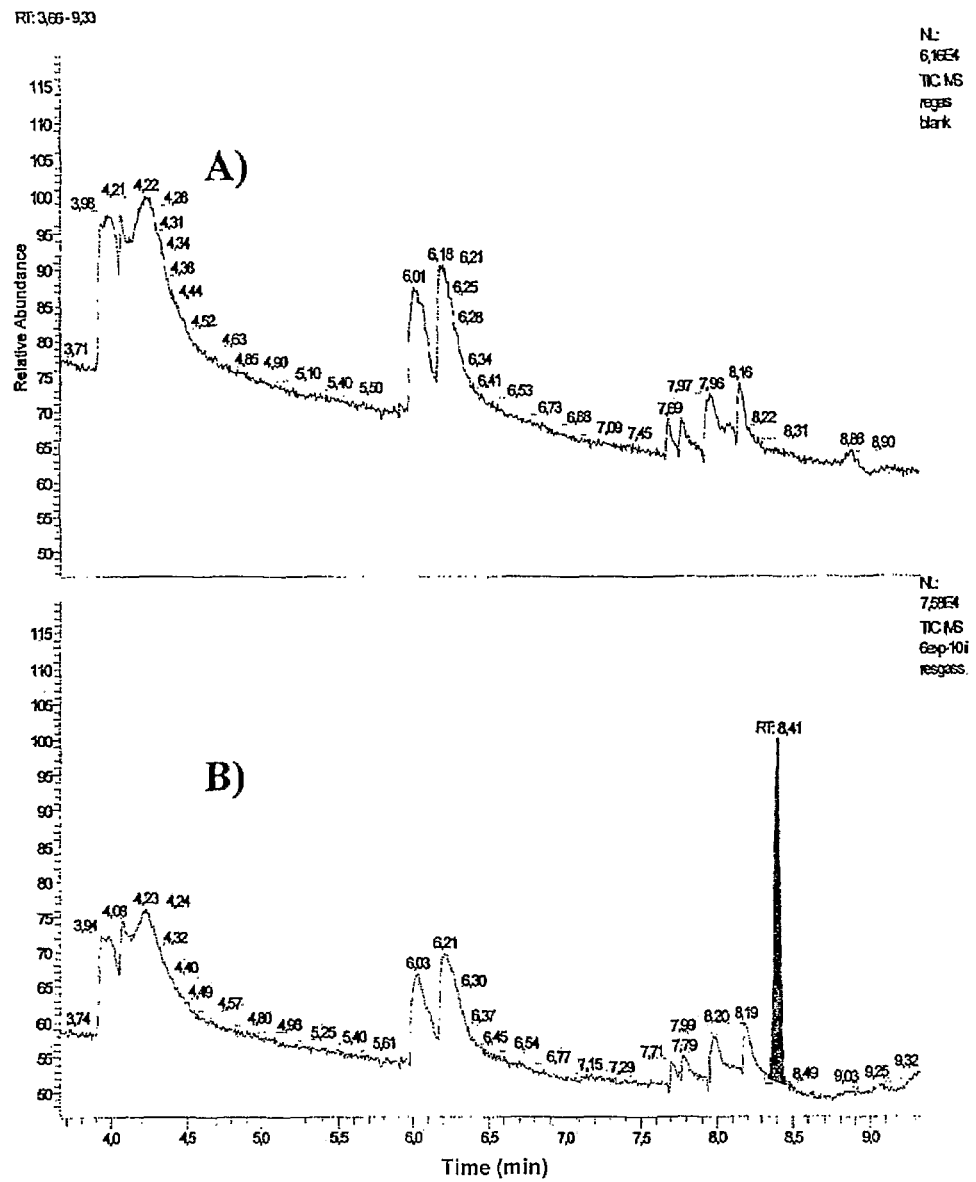

FIG. 8 shows two chromatograms from GC-MS analysis where the detector gauge measurement (y-axis) is plotted as a function of time (x-axis). One chromatogram (A) is from the analysis of a blind sample of reservoir gas, whereas the other (B) is from the analysis of reservoir gas added TMG at a concentration of $6 \times 10^{-10}$ l/l.

Figure 9:
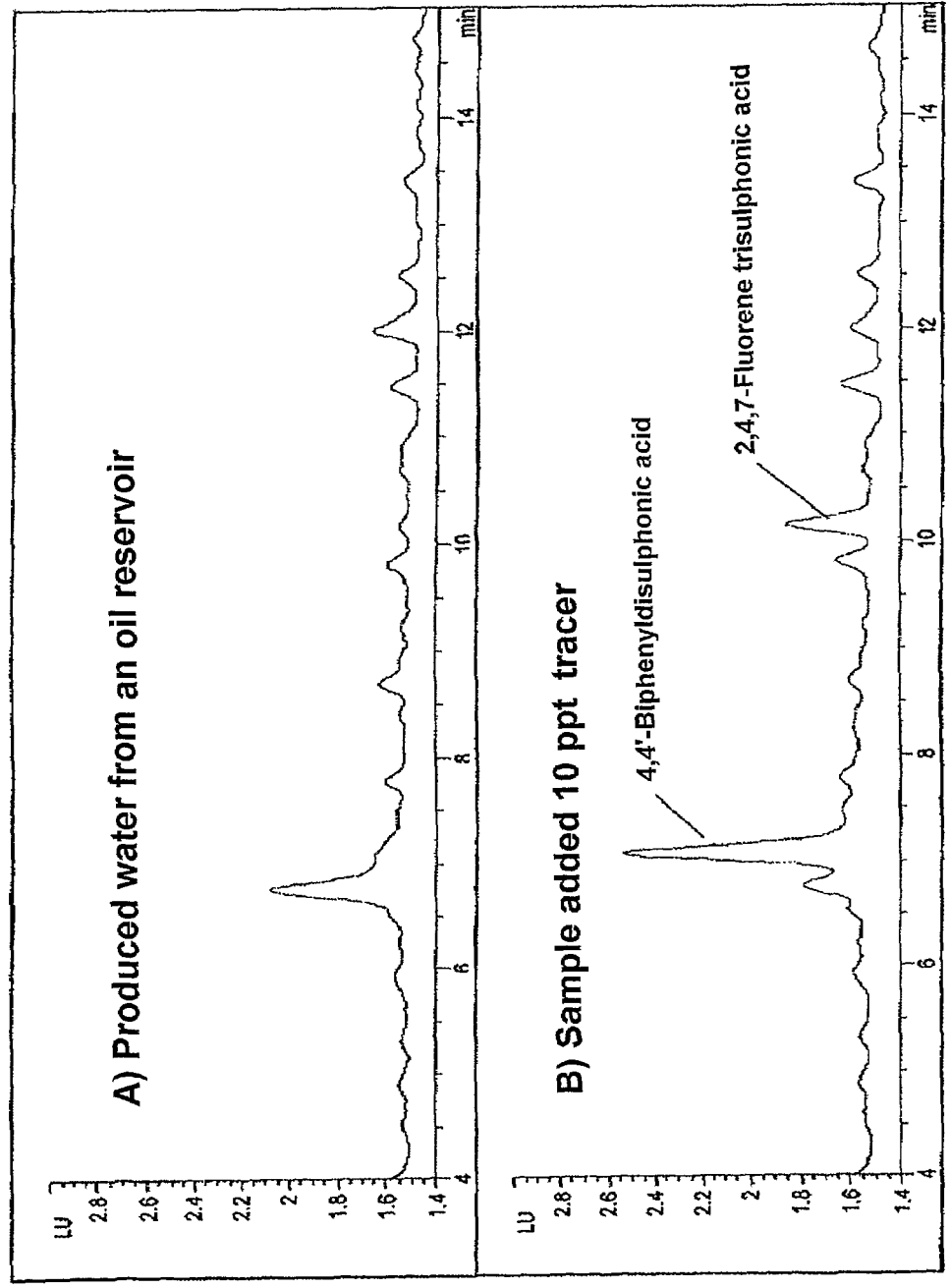

FIG. 9 shows two graphic representations of retention time (x-axis) versus response from a fluorescence detector (y-axis) after HPLC-FLD analysis of (A): produced water from an oil well, and B): the same sample as from A) with added 10 μg 4,4'-biphenyl disulphonic acid disodium salt per cubic meter (10 ppt) and 10 μg/m³ of a composition of fluorene sulphonic acids which mainly consisted of 2,4,7-fluorene trisulphonic acid.

Figure 10:
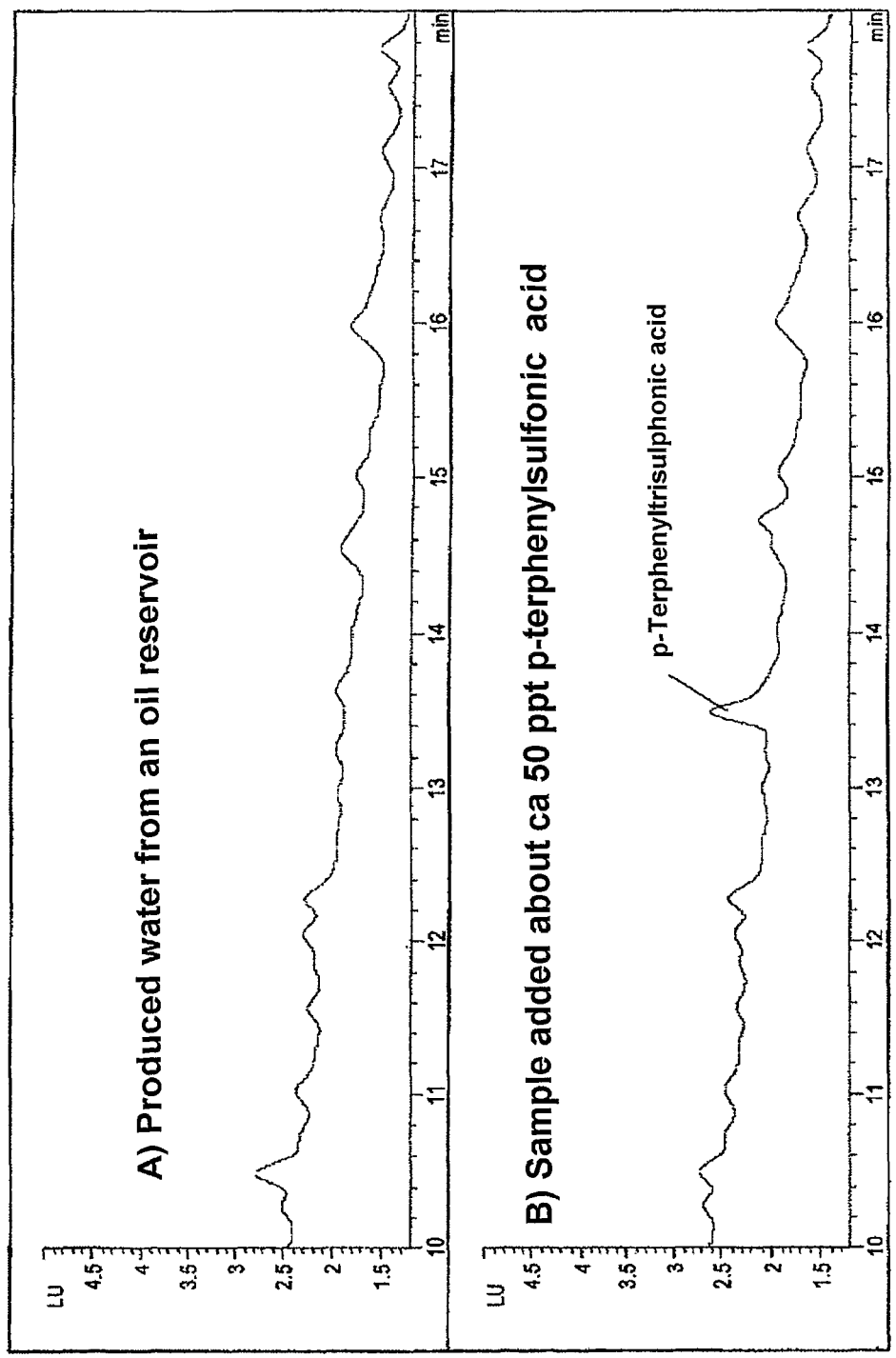

FIG. 10 shows two graphic representations of retention time (x-axis) versus response from a fluorescence detector (y-axis) after HPLC-FLD analysis of A): produced water from an oil well and B): the same sample as A) added 50 μg p-terphenyl trisulphonic acid per cubic meter (50 ppt).

Figure 11:
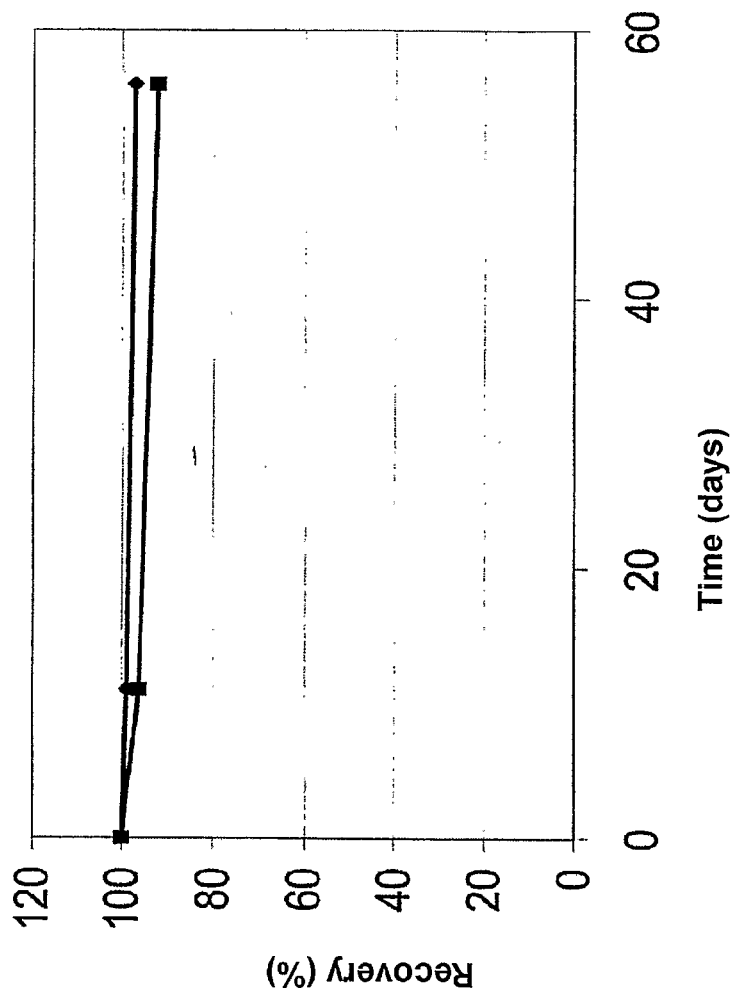

FIG. 11 shows a graphic representation of a thermal stability test of 4,4'-biphenyl disulphonic acid heated to 195° C. The tracer material was dissolved in artificial formation water and heated in tubes of quartz that were molten shut and containing Berea sandstone or limestone and where the air had been replaced with argon.

FIG. 12 shows general structural formula for isomers of biphenyl disulphonic acid, fluorene disulphonic acid and p-terphenyl trisulphonic acid.

Another aspect of the invention concerns the use of organometallic compounds wherein the element germanium makes up the metallic element, as a tracer for measuring gas-streams in oil and gas reservoirs or other uses where tracers for gas or oil are used. The trace element molecules may have hydrogen and/or different organic groups such as methyl, ethyl, propyl and vinyl groups or a combination thereof bound to the germanium atom. These compounds will probably have a lower potential for heating of the atmosphere (GWP) than perfluorinated carbons (PFK) being widely used as tracers for gas. They are consequently considered as more environmentally friendly than PFK, and they are neither regarded as toxic for live organisms. The tracers may be detected at low concentrations through the aid of gas chromatography (GC) with a specific germanium detector, gas chromatography mass spectrometry (GC-MS) and gas chromatography with inductively coupled plasma mass spectrometry (GC-ICP-MS).

BACKGROUND

This aspect of the invention concerns chemical compounds wherein the element germanium is bound to hydrogen and/or different organic molecular groups and the use thereof for measuring or studying streams of gas in oil and gas reservoirs or in other situations wherein trace elements for gas are used.

The Institute for Energy Technology (IFE) has worked with the development of trace element technology for industrial purposes since the nineteen sixties. Since the beginning of the nineteenth eighties there has been a focus on the development of this technology to be used in the oil and gas industry. The main purpose of inter-well (well-to-well) trace element investigation is to map the current fields in the reservoir and measure qualitatively and quantitatively the current connections between injection and production wells. The data from the trace element investigations in combination with common production data, pressure measurements and information from well logging provides the best available basis for evaluating the pattern of the dynamic gas-currents and thus the optimal exploitation of the reservoir. IFE uses today mainly organic trace substances such as perfluorinated carbons (PFK) and radioactively labelled compounds in trace element investigations of gas or oil and condensate. The environmental authorities in Norway have expressed that these compounds gradually should be phased out and be replaced by more environmentally friendly trace substances even if PFK has been proven to be almost completely degraded through combustion. Radioactive substances are also expressively to be avoided if completely adequate non-radioactive alternatives exist. There is also an ever-present demand for new trace substances to be used in oil reservoirs as older substances have been used in the wells. Voroncov et al. have reported low toxicity for organic germanium compounds.

Stability tests performed by IFE have shown that tetramethyl germanium (TMG) was stable at 120° C. over a period of six months in steel cylinders that were pressurized to 40 bars with nitrogen and which also contained san and water. Many of the other organic germanium compounds are presumed to possess corresponding properties with respect to thermal stability. TMG may per today be detected down to a level of $10^{-10}$ l/l (100 ppt) through the aid of GC-MS with up-concentration of 20 ml reservoir gas, and an even lower detection limit is expected to be obtained by using GC with a detector being specific for germanium or through the aid of GC-ICP-MS.

The expression "possible isomers" is in the present context meant to be compounds that both theoretically and practically may be synthesized by said compounds.

The expression "salts thereof" is meant to include all salts of organic and inorganic bases that will form a salt with acid function of the compounds defined supra in the disclosure. Such bases are compounds that will form suitable positively charged counter-ions that react with the acid function of the relevant biphenylmono- and polysulphonic acids, the fluorenemono- and polysulphonic acids and the p-terphenylmono- and polysulphonic acids disclosed supra.

The invention claimed is:

1. A method for tracing, surveying, monitoring, and/or measuring the movement of aqueous fluids in aqueous and/or non-aqueous media, comprising the addition of one or more chemical compound(s) selected from biphenylmono- and polysulphonic acids and salts thereof, fluorenemono- and polysulphonic acids and salts thereof, and p-terphenylmono- and polysulphonic acids and salts thereof into said aqueous fluids, wherein the chemical compound(s) is detected in said aqueous or non-aqueous media through analysis using analytical techniques such as high performance liquid chromatography with fluorescence detection and/or liquid chromatography-electrospray mass spectrometry such that the movement of said chemical compound(s) are traced, surveyed, monitored, and/or measured in said aqueous or non-aqueous media.

2. The method according to claim 1, wherein the aqueous fluids to be traced, surveyed, monitored and/or measured is/are present in an oil reservoir or well.

3. The method according to claim 1, wherein the aqueous fluids to be traced, surveyed, monitored and/or measured is/are present in a hydrothermal reservoir or well.

4. The method according to claim 1, including tracing, surveying, monitoring, and/or measuring the aqueous fluids that is/are present in an industrial process.

5. The method according to claim 1, wherein the aqueous fluids to be traced, surveyed, monitored and/or measured is/are present in a hydrological study.

6. The method according to claim 1, wherein one or more of the hydrogen atoms attached to the ring system of the biphenylmono- and polysulphonic acids and salts, the fluorenemono- and polysulphonic acids and salts and p-terphenyimono- and polysulphonic acids and salts is substituted by one or more amino, hydroxyl and/or methyl groups.

7. The method according to claim 2, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

8. The method according to claim 3, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

9. The method according to claim 4, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

10. The method according to claim 5, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

11. The method according to claim 4, including tracing, surveying, monitoring, and/or measuring the aqueous fluids that is/are present in tracer studies monitoring the movement of 1,2-ethanediol.

12. The method according to claim 11, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

13. The method according to claim 5, including tracing, surveying, monitoring, and/or measuring the aqueous fluids that is/are present in sub-water or sub-aqueous streams or currents such as water-based fluids such as formation water, production water injected into petrol or oil reservoirs, ground water, and geothermic brines.

14. The method according to claim 13, wherein one or more of the hydrogen atoms attached to the ring system of the biphenylmono- and polysulphonic acids and salts, the fluorenemono- and polysulphonic acids and salts and p-terphenylmono- and polysulphonic acids and salts is substituted by one or more amino, hydroxyl and/or methyl groups.

15. The method according to claim 1, wherein the chemical compound(s) is detected in said aqueous and/or non-aqueous media through analysis using gas chromatography with a specific germanium detector.

16. The method according to claim 1, wherein the chemical compound(s) is detected in said aqueous and/or non-aqueous media through analysis using gas chromatography mass spectrometry.

17. The method according to claim 1, wherein the chemical compound(s) is detected in said aqueous and/or non-aqueous media through analysis using gas chromatography with inductively coupled plasma mass spectrometry.

* * * * *